(12) United States Patent
Akutsu et al.

(10) Patent No.: US 10,094,748 B2
(45) Date of Patent: Oct. 9, 2018

(54) SPECIMEN TRANSFER DEVICE AND SYSTEM

(71) Applicant: HITACHI HIGH-TECHNOLOGIES CORPORATION, Tokyo (JP)

(72) Inventors: Masashi Akutsu, Tokyo (JP); Naoto Tsujimura, Tokyo (JP); Kenichi Takahashi, Tokyo (JP); Hiroshi Ohga, Tokyo (JP); Osamu Watabe, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 546 days.

(21) Appl. No.: 14/353,798

(22) PCT Filed: Dec. 5, 2012

(86) PCT No.: PCT/JP2012/081439
§ 371 (c)(1),
(2) Date: Apr. 24, 2014

(87) PCT Pub. No.: WO2013/099538
PCT Pub. Date: Jul. 4, 2013

(65) Prior Publication Data
US 2014/0294699 A1    Oct. 2, 2014

(30) Foreign Application Priority Data
Dec. 28, 2011 (JP) ................................ 2011-287261

(51) Int. Cl.
*G01N 1/28* (2006.01)
*G01N 35/04* (2006.01)

(52) U.S. Cl.
CPC ............... *G01N 1/28* (2013.01); *G01N 35/04* (2013.01); *G01N 2035/041* (2013.01); *G01N 2035/0412* (2013.01); *G01N 2035/0465* (2013.01)

(58) Field of Classification Search
CPC ............... G01N 1/28; G01N 2035/041; G01N 2035/0412; G01N 35/04; G01N 2035/0465; Y10T 436/114165
See application file for complete search history.

(56) References Cited

U.S. PATENT DOCUMENTS 4,268,477 A  *  5/1981  Herzstark .......... G01N 35/0095
                                                   141/130
5,150,795 A      9/1992  Nakayama et al.
(Continued)

FOREIGN PATENT DOCUMENTS

DE        19912211 A1    12/2001
JP        62-232570 A    10/1987
(Continued)

OTHER PUBLICATIONS

Chinese Office Action received in corresponding Chinese Application No. 201280064969.4 dated Feb. 28, 2015.
(Continued)

*Primary Examiner* — Benjamin R Whatley
(74) *Attorney, Agent, or Firm* — Mattingly & Malur, PC

(57) ABSTRACT

A specimen transfer device having high flexibility is implemented, where a specimen can be transferred between carriers purposed for different kinds of conveyance without decreasing processing speed for the specimen. A plurality of trays that can retain specimen carriers of a transfer destination is provided, and these trays can be freely grouped, and therefore, while a carrier is fed from a tray, a specimen is automatically executed to a carrier in a different tray.

10 Claims, 6 Drawing Sheets

(56) References Cited

U.S. PATENT DOCUMENTS

| | | | | |
|---|---|---|---|---|
| 6,117,683 A | * | 9/2000 | Kodama | G01N 35/00584 422/65 |
| 6,141,602 A | * | 10/2000 | Igarashi | G01N 35/0092 422/561 |
| 6,255,614 B1 | * | 7/2001 | Yamakawa | G01N 35/04 209/509 |
| 2004/0053414 A1 | * | 3/2004 | Devlin, Sr. | G01N 35/0092 436/43 |
| 2009/0142844 A1 | * | 6/2009 | Le Comte | G01N 35/00594 436/8 |
| 2010/0028124 A1 | | 2/2010 | Lackner et al. | |
| 2010/0124518 A1 | * | 5/2010 | Koike | G01N 35/026 422/65 |
| 2010/0330609 A1 | * | 12/2010 | Nagai | G01N 35/0092 435/29 |
| 2011/0158850 A1 | * | 6/2011 | Pedrazzini | B01L 9/02 422/65 |
| 2013/0061693 A1 | * | 3/2013 | Sasaki | G01N 35/00732 73/863.01 |
| 2013/0123089 A1 | * | 5/2013 | Johns | B01D 21/262 494/37 |

FOREIGN PATENT DOCUMENTS

| | | |
|---|---|---|
| JP | 03-041365 A | 2/1991 |
| JP | 04-074965 A | 10/1992 |
| JP | 05-142232 A | 6/1993 |
| JP | 07-280815 A | 10/1995 |
| JP | 10-239321 A | 9/1998 |
| JP | 11-316238 A | 11/1999 |
| JP | 2002-40034 A | 2/2002 |
| JP | 2002-090374 A | 3/2002 |
| JP | 2004-061136 A | 2/2004 |
| WO | WO 2011148897 A1 * 12/2011 ....... G01N 35/00732 |

OTHER PUBLICATIONS

Extended European Search Report received in corresponding European Application No. 12862127.3 dated Jul. 28, 2015.

* cited by examiner

SPECIMEN UNIT MODE
ALL POSITIONS TRANSFERRED WITHIN TIME-OUT PERIOD

SPECIMEN UNIT MODE
TRANSFER NOT COMPLETED WITHIN TIME-OUT PERIOD

SPECIMEN UNIT MODE
TIME-OUT VALUE CHANGED FOR URGENT SPECIMEN OR THE LIKE

SPECIMEN TRANSFER DEVICE AND SYSTEM

TECHNICAL FIELD

The present invention relates to a specimen processing system suitable for automatically performing a specimen examination in a clinical examination field, particularly relating to a system including a mechanism that transfers specimens.

BACKGROUND ART

In a hospital or a clinical laboratory, specimens such as blood and urine are analyzed for clinical examination, but the specimen from a patient is not always provided as it is for analysis and in most of the cases pretreatment for the analysis is applied to the specimen. The system that automates such pretreatment and analysis is a specimen processing system.

In recent years, the specimen examination has been diversified, and accordingly, a plurality of examinations such as hematologic examination, biochemical examination, and immunity examination is executed in the case of only performing the examination so-called blood examination. The above mentioned specimen processing system is developed so as to perform the plurality of examination items massively and automatically in a short time.

In a general specimen processing system, a bar code label is pasted on a specimen container containing a specimen collected from a patient, and the specimen container is fed to the specimen processing system from a rack supply unit, held in a box-shaped carrier called a rack.

Therefore, in the rack supply unit, the bar code label pasted on the specimen container is read and the specimen container is conveyed to each kind of processing unit that applies necessary pretreatment based on the information, thereby executing the pretreatment.

After that, the rack finished with the pretreatment for the specimen is conveyed to the most relevant analyzing device in accordance with individual examination items, and then the analysis is executed. An example of such a system is disclosed in PTL 1, for example.

CITATION LIST

Patent Literature

PTL 1: JP 7-280815 A

SUMMARY OF INVENTION

Technical Problem

By the way, the most difficult problem in the above-described specimen processing system is a form of the carrier in order to integrally connect a pretreatment system for the specimen to an analyzing system as one specimen processing system. In fact, the carriers are developed and manufactured in unique forms in the respective systems. For example, there is a case where the pretreatment system is formed of a system conveying one specimen container while the analyzing system is formed of a system conveying five specimen containers.

For this reason, in a connecting point between the analyzing system and the pretreatment system, it is necessary to provide a transfer device between the carriers, e.g., from the carrier holding one specimen container to the carrier holding five specimen containers. However, actually there are many cases in which a plurality of analyzing systems is connected to the pretreatment system, and it is necessary to perform transferring action in parallel to the carriers of the plurality of analyzing systems. In other words, feeding the carriers to the plurality of analyzing systems may decrease processing capacity of an entire system in the case where one carrier cannot be transferred while the other carrier is being fed.

Also, in the actual examination system, there may be a case where connected analyzing systems are not equivalent and are different kinds of analyzing devices, such as an analyzing device to measure a biochemical examination item, and an analyzing device to measure an immunological examination item. In this case, the carriers may not be constantly conveyed to the respective analyzing systems at the same ratio, more specifically, a large number of specimens are conveyed to one of the analyzing systems while a small number of specimens are conveyed to the other analyzing system.

Further, in the analyzing system to which a specimen is conveyed, it is also necessary to read a bar code of the specimen to recognize the specimen. However, in a general analyzing system, there is a problem in which the bar code cannot be correctly read and the specimen cannot be recognized when a bar code of a specimen is not oriented in a reading direction of the bar code reader.

In view of the above situation, the object of the present invention is to implement a specimen processing system having high flexibility, in which specimen containers can be conveyed via plural kinds of racks without decreasing a specimen processing speed of the entire system.

Solution to Problem

In view of the above problem, characteristic configurations according to the present invention are as follows. More specifically, the specimen transfer device is characterized in including a carrier that transfers one or more specimen containers, a plurality of trays configured to retain the carrier, a transfer unit configured to transfer a specimen container to the carrier on the tray, wherein the specimen transfer device also includes a unit configured to group at least two trays out of the plurality of trays, and a control unit configured to execute control such that, when the transfer unit transfers specimen containers to a carrier retained on a tray and the carrier becomes fully loaded, transference of a next specimen container to be transferred to the carrier on the tray is switched to a carrier retained in a different tray allocated to a same group.

Further, the specimen transfer device having the above-described characteristics may be incorporated between a pretreatment device and an analyzing device to form a system.

The transfer device according to the present invention enables conveying action during transferring action by adopting the above described configurations, and the respective analyzing system can receive the carriers in which the specimens are uniformly oriented in the same direction, thereby achieving to improve total throughput.

Advantageous Effects of Invention

According to the present invention, in a system where a pretreatment system is connected to a plurality of analyzing systems, it is not necessary to temporarily stop transferring action while a carrier is conveyed to one analyzing system, and this can implement the transfer device having high processing capacity. Additionally, in the analyzing system, a bar code can be read regardless of the orientation of the specimens being conveyed.

DESCRIPTION OF EMBODIMENTS

Exemplary embodiments of the present invention will be described below.

First Embodiment

An embodiment according to the present invention will be described with reference to the drawings.

Figure 1:
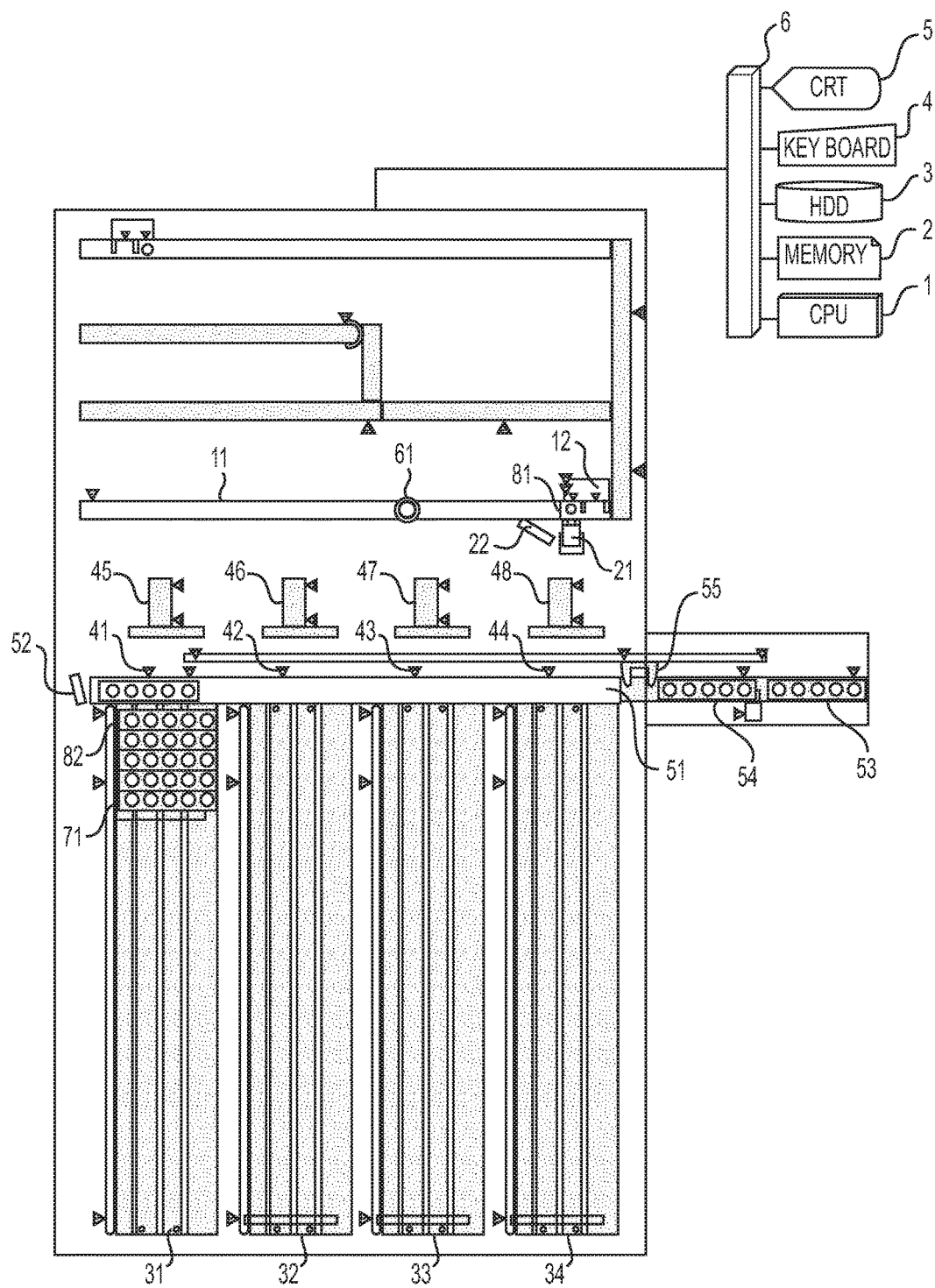
FIG. 1 is a diagram illustrating a configuration of a specimen transfer device according to an embodiment of the present invention.

FIG. 1 is a block diagram of a transfer device in which the embodiment of the present invention is applied. Here, it is assumed that a transfer device connects a pretreatment system conveying one specimen container and an analyzing system conveying five specimen containers, in which the specimen container finished with the pretreatment is removed from a carrier of the pretreatment system and transferred to a carrier used in the analyzing system.

A reference sign 61 indicates a carrier conveyed inside the pretreatment system, and one specimen container 91 can be placed in this carrier. A reference sign 71 indicates a carrier conveyed inside the analyzing system, and five specimen containers 91 can be placed in this carrier.

This is an exemplary case, and therefore the carrier 61 conveyed inside the pretreatment system may also convey a plurality of specimen containers 91. Further, the carrier 71 conveyed inside the analyzing system is required to be at least capable of conveying a plurality of specimen containers 91.

In the analyzing system connected to the transfer device according to the present invention, generally a recognizing unit to recognize a specimen reads bar code information 92 of a specimen as well as bar code information 72 of a carrier. However, there is a recognizing unit that does not read the bar code information 92 of the specimen and only reads the bar code information 72 of the carrier to recognize the specimen at a position inside the carrier.

Therefore, information which associates carrier information with a transfer position of the specimen is important key information for recognition.

A reference sign 11 indicates a conveyance line for conveying the carrier 61 that holds one specimen container 91 to be conveyed inside the pretreatment system. The carrier 61 does not have a self-advancing function in itself. The conveyance line 11 is formed of a belt line, and therefore, the carrier 61 existing on the conveyance line 11 can be conveyed by rotary drive of the belt line. Since the conveyance line is formed of the belt line, even when a plurality of carriers 61 exists on one belt line, the carriers can be conveyed.

A reference sign 12 indicates a stopper mechanism. The stopper mechanism is mounted on the conveyance line 11, and capable of stopping conveyance of the carrier 61 being conveyed. Also, even when the plurality of the carriers 61 successively stagnates on the conveyance line 11, the carriers can be separated one by one.

Reference signs 31, 32, 33 and 34 indicate trays that retain a plurality of carriers where five specimen containers 91 conveyed inside the analyzing device can be placed. According to the present embodiment, four trays are included, but the number of trays is not limited thereto as long as it is plural. A plurality of carriers 71 can be contained inside one tray.

The carriers 71 on the trays 31, 32, 33 and 34 are fed one by one from the trays and recognized by detectors 41, 42, 43 and 44.

An ID of the carrier 71 is needed to be recognized before starting the transferring action to create the above-mentioned associated information.

A carrier conveyance mechanism 55 on the conveyance line 51 once conveys the carrier 71 placed on the recognized tray to a bar code reader 52 for a transfer destination carrier. After reading the carrier bar code information 72 of the conveyed carrier 71 and recognizing the bar code information of the carrier, the carrier is conveyed to the front of the tray from which the carrier has been fed, by again using the same carrier conveyance mechanism 55. At this point, the carriers are put back to the trays by pushing-back mechanisms 45, 46, 47 and 48.

After the transferring action, the carrier is conveyed to a transfer destination carrier standby position 54 and an analyzing device handover position 53 via the conveyance line 51. Subsequently, reading the carrier bar code information 72 for a next empty carrier 71 is performed in the same manner.

For this reason, the conveyance line 51 has a mechanism whereby the carrier 71 is conveyed bidirectionally. In the case where the carrier 71 falls in a waiting state on the conveyance line 51, the carrier 71 fed from a different tray cannot be conveyed. Therefore, the pushing-back mechanisms 45, 46, 47 and 48 are configured to make the carrier 71 to wait on the tray.

When the analyzing device handover position 53 and the standby position 54 are not empty, conveying action for the carrier 71 finished with the transferring action is not executed. The reason is that there is a case where analyzing device side is too busy to accept a new carrier.

This can temporarily absorb a difference of processing capacity between the analyzing device and the pretreatment device.

The carrier 61 having been conveyed inside the pretreatment system is stopped at a transfer source position 81 by the stopper mechanism 12. After that, the bar code information 92 of the specimen is read by the bar code reader 22, rotating the specimen container 91 with a rotation mechanism 21.

The read bar code information 92 of the specimen is sent to a control computer via an interface 6. In a storage device 3 inside the control computer, analysis item information necessary for the specimen associated with the bar code information of each specimen is preliminarily stored. The transfer destination tray of the specimen container is, accordingly, determined by searching the information stored inside the storage device 3 based on the bar code information 92 that has been read. Note that the transfer destination tray is generally allotted in accordance with a purpose of conveyance of the specimen container, and further is associated with a position of the bar code information 72 of the carrier.

The information related to the transfer destination tray is also notified to the transfer device via the interface 6 in the same manner. The specimen container is transferred to a transfer destination position 82 from the transfer source position 81 based on this information. A transfer mechanism used at this point is a transfer X-Y-Z mechanism 111 and a chuck mechanism 112 configured to move in X, Y and Z axes directions.

The transfer destination position 82 exists on the trays 31, 32, 33 and 34. The plurality of carriers 71 are retained on the trays, but the transfer destination position is a position where the carrier 71 located closest to the conveyance line on the tray retains the specimen containers. Additionally, the position is required to be at least free from interfering with the carrier 71 while the carrier 71 is moving on the conveyance line 51.

Figure 2:
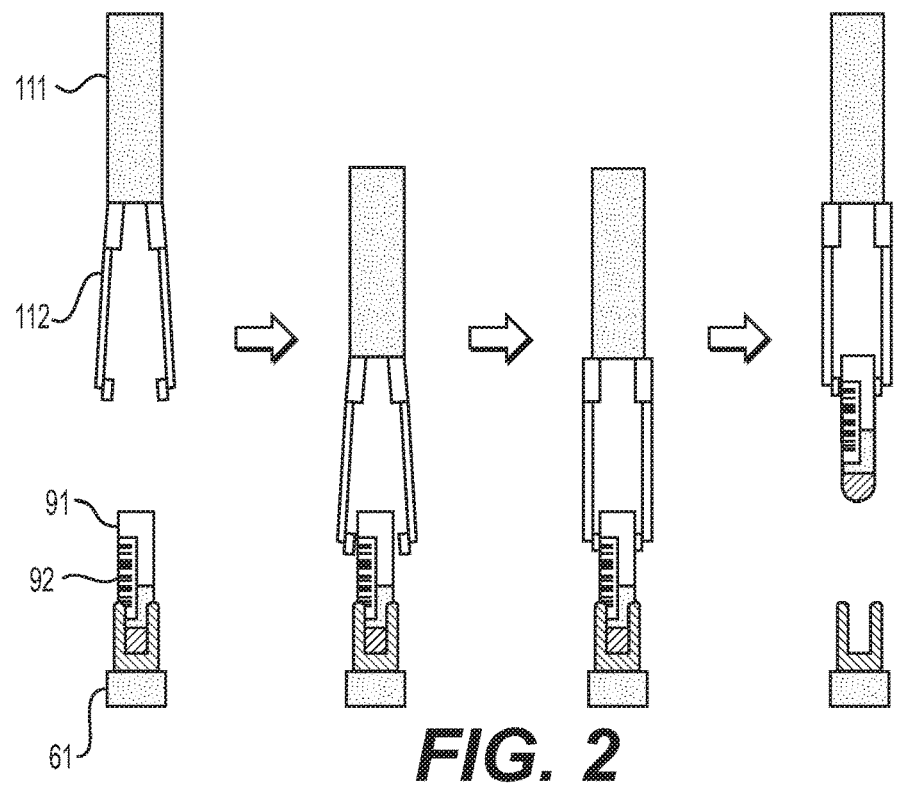
FIG. 2 is a view illustrating removing operation for a specimen.
Figure 3:
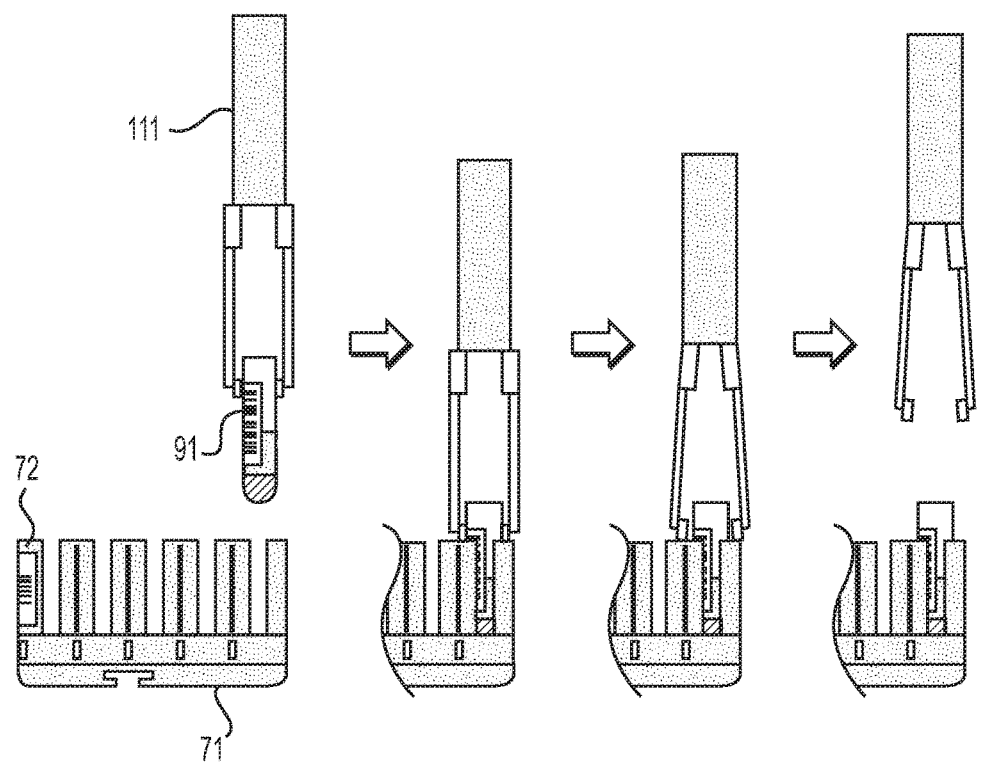
FIG. 3 is a view illustrating placing operation for a specimen.

Next, transferring action for the specimen container will be described using FIGS. 2 and 3.

The transfer X-Y-Z mechanism 111 moves down in Z direction from right above of the specimen container 91 on the carrier 61 with the chuck mechanism 112 in an open state. When the X-Y-Z mechanism 111 reaches to a graspable position, the chuck mechanism 112 is closed and removes the specimen container 91 from the carrier 61 by elevating in Z direction.

Keeping this state, the X-Y-Z mechanism 111 moves in X and Y directions and then moves to above the carrier 71. While grasping the specimen container 91, the X-Y-Z mechanism 111 moves down in Z direction and opens the chuck mechanism 112, and then places the specimen container 91 on the carrier 71 by elevating in Z direction.

Note that, according to the above described embodiment, a storage medium carrier 71 storing the ID is the bar code, but an IC tag such as an RFID may be used as well. In this case, an RFID antenna is to be provided on the conveyance line for transfer destination carrier 51 instead of the bar code reader 52 for a transfer destination carrier.

According to the present embodiment, the bar code information of the carriers 71 contained in the plurality of trays can be read by one carrier bar code reader 52, thereby reducing the cost for mechanism.

Further, according to the present embodiment, the case where the specimen is transferred from the transfer source carrier 61 to the transfer destination carrier 71 has been described above; however, the present invention is not limited thereto and applicable to a case where a container is transferred to a carrier used for conveying the container. For instance, the transfer source carrier may be a specimen tray or the like where the specimen containers are arranged in an array form, or the number of specimens that can be transferred by the transfer destination carrier may be five or less, or five or more.

Second Embodiment

Figure 4:
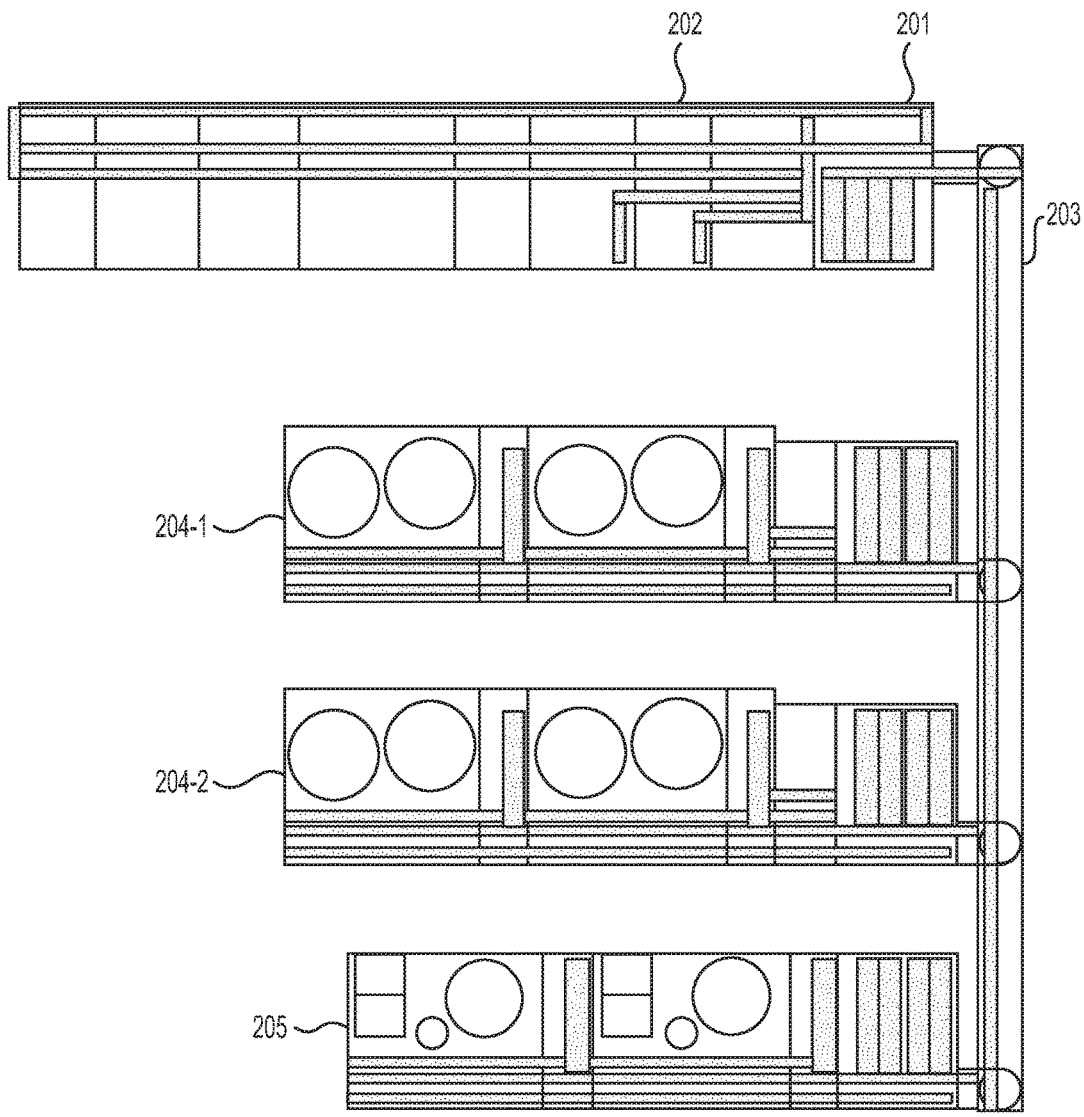
FIG. 4 is a configuration of a specimen processing system according to an embodiment of the present invention.

A specimen processing system that connects a pretreatment system to an analyzing system by using a specimen transfer device will be described with reference to FIG. 4.

A reference sign 202 indicates the pretreatment system. Here, the pretreatment system is a system that processes a carrier 61 in which one specimen container 91 can be placed, and also performs pretreatment required for analyzing a specimen examination. More specifically, the pretreatment system is formed of, for example, a centrifugal separation device, a plug-opening device, a daughter specimen container preparation device, a specimen dispensing device, and so on.

A reference sign 203 indicates a conveyance line system. Here, the conveyance line system is configured to handle the carrier 71 in which the plurality of specimen containers 91 finished with the pretreatment is placed, and has a function to perform conveyance to an analyzing system, selecting from among analyzing systems 204-1, 204-2 and 205.

The reference signs 204-1, 204-2 and 205 indicate the analyzing systems. For instance, the reference signs 204-1 and 204-2 are the same analyzing systems and the reference sign 205 is a different analyzing system. More specifically, the reference signs 204-1 and 204-2 are biochemical analyzing systems, and the reference sign 205 is an immunological examination analyzing system or the like.

As for the carriers used in both systems, the pretreatment system 202 adopts a system conveying the carrier 61 where one specimen container 91 is placed, and the analyzing systems 204-1, 204-2 and 205 adopts systems each conveying the carrier 71 where five specimen containers 91 are placed. Therefore, the specimen containers 91 finished with the pretreatment are required to be transferred from the carrier 61 to the carrier 71.

The above systems, therefore, are connected with a transfer device 201, thereby absorbing a difference between the carriers.

The detail of the transfer device 201 in the present system is as illustrated in FIG. 1, and a plurality of trays is included. Here, an example including four trays will be described. In an actual system, the carriers are classified in the transfer device for each of the analyzing systems, and therefore the four trays and the carriers retained in the respective trays are allocated to the analyzing systems 204-1, 204-2 and 205.

For instance, trays 31, 32 and 33 are allocated to the biochemical analyzing system having a large number of specimens, and a tray 34 is allocated to the immunological examination analyzing system having a small number of specimens.

Since the specimen finished with the pretreatment is intermittently conveyed from the pretreatment system to the transfer device, transfer requests to the biochemical analyzing system having a large number of requests for analyzing specimens are continuously made. When the transfer requests are continuously made to the carriers 71 on the same tray, the carriers 71 become fully loaded quickly. The fully-loaded carriers 71 are discharged to a conveyance line 51.

While the discharging operation, the fully-loaded carriers are conveyed to the conveyance line 51 and also a next carrier is transferred to a transfer position 82 on the tray. At this point, it is necessary to convey the carrier 71 to a bar code reader for transfer destination carrier 52 to recognize bar code information of the carrier 71, and also it is necessary to return the carrier 71 for which the bar code has been read to the transfer position 82. For this reason, the tray becomes unusable and transfer of the specimen containers is stagnated until the next carrier is set at the transfer position 82 and transferring the specimen containers can be restarted.

Therefore, as for the biochemical examination system having a large number of the requests as described above, a group allocated with a plurality of trays is made such that transference is automatically switched to a carrier in a different tray when carrier transfer is finished with one tray. This may implement continuous specimens transfer and prevents decrease of processing capacity.

Also, the plurality of carriers can be set in the tray, and once a next carrier is set, transference of the specimen containers to the tray can be restarted even when one carrier is fully loaded and discharged to the conveyance line 51.

However, the tray allocated to the biochemical examination system having a large number of requests, the carriers may be severely worn out and there may be a case in which all of the carriers on the tray are conveyed. In the case where the system recognizes such situation, the transfer destination is controlled to automatically switch to a different tray allocated to the same group. While the transferring operation is temporarily switched to the different tray, a notification indicating emptiness of the tray is sent to an operator. When replenishment of a rack in the tray is recognized, transfer of the specimen containers to the tray will be permitted again. With this control, the transferring operation can be continued without decreasing processing efficiency.

Meanwhile, in the case of executing allocation to the analyzing system having a small number of requests, a group is allocated with one tray. However, processing capacity may not be decreased in a normal operation even at when the above replacement is executed because specimens transferring action is more likely to be performed in other group.

Figure 8:
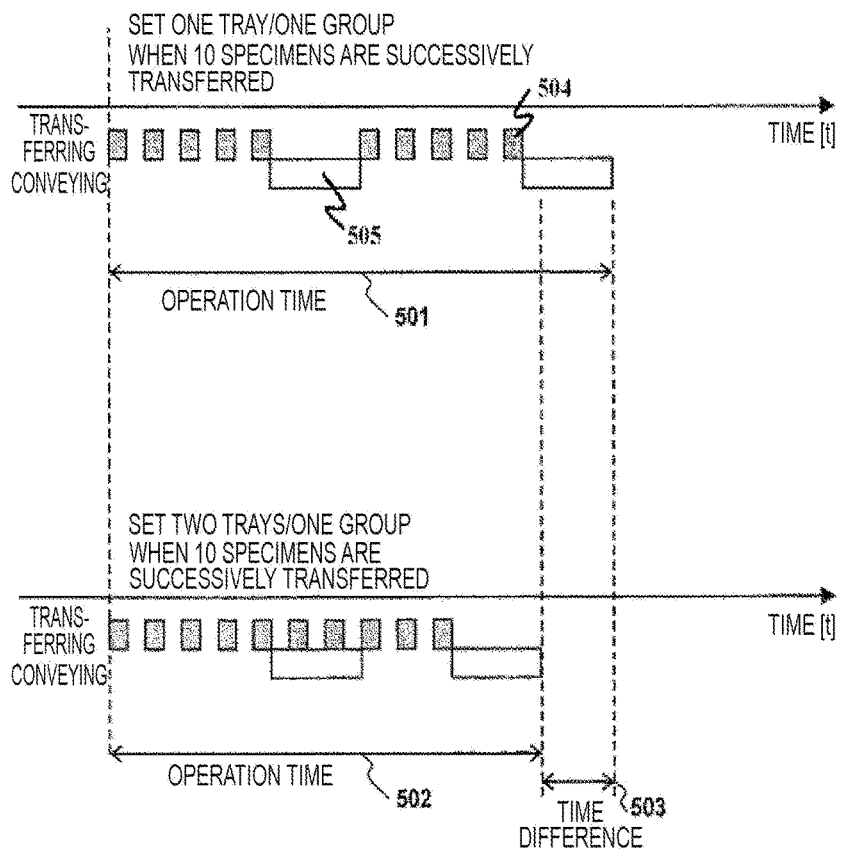
FIG. 8 is a diagram for describing transferring action in the case where grouping is applied.

Functions of this grouping will be described with reference to FIG. 8.

First, a description will be given for a case where no group is formed, more specifically, the case where operation is executed only with one tray. In this case, when the specimen containers 91 are successively transferred to the carrier on the tray (transferring timing 504), it is necessary to discharge the fully-loaded carrier 71 from the tray and a next carrier has to be placed at the transfer position. For that, the transferring action itself is required to be temporarily stopped because it is necessary to discharge the fully-loaded carrier to the conveyance line 51, and further the carrier 71 to be used next has to be positioned at the transfer position 82 for preparation after the ID information of the carrier 71 is read by the bar code reader 52 for a transfer destination carrier (transfer preparation timing 505). The temporary stop of the transferring action while executing the successive transferring operation for the specimens causes decrease of processing capacity (operation time difference 503).

On the other hand, in the case of operating with two trays allocated to one group, the carrier 71 starts to be conveyed from a tray to the conveyance line for transfer destination carrier 51 when the carrier 71 on the other tray is fully loaded. Next, while the transferring operation for the former carrier 71 is executed, the carrier 71 that receives transfer of the specimen container is once conveyed to the conveyance line 51 for the transfer destination carrier and ID reading operation is executed by the bar code reader for transfer destination carrier 52. With this configuration, the specimen container 91 to be transferred next can be transferred to a carrier on the other tray after the former carrier 71 is fully loaded and conveyed, and therefore the temporary stop of transferring action becomes unnecessary. In other words, decrease of processing capacity can be prevented by executing the processing among a plurality of trays in parallel.

Third Embodiment

Figure 6:
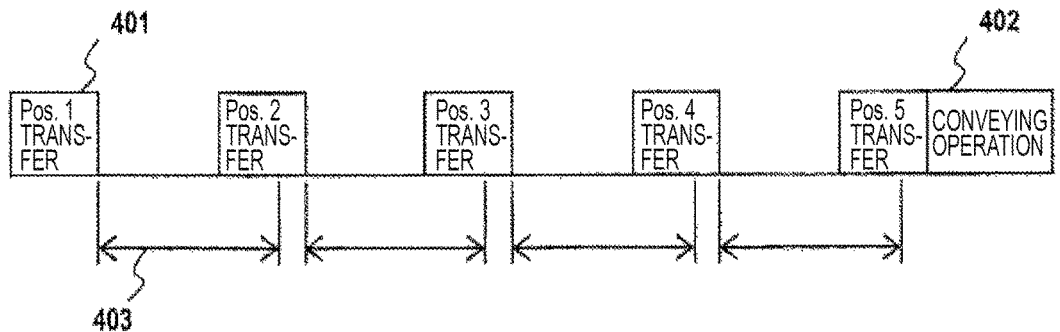
FIG. 6 is a diagram for describing operation of time-out control mode per specimen unit.
Figure 6:
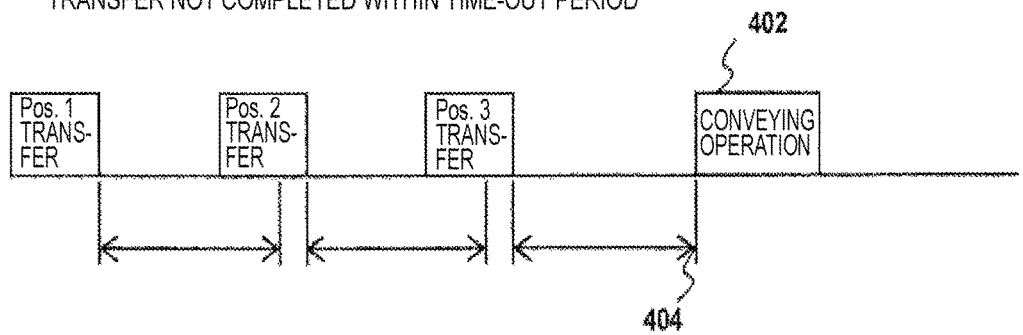
Figure 6:
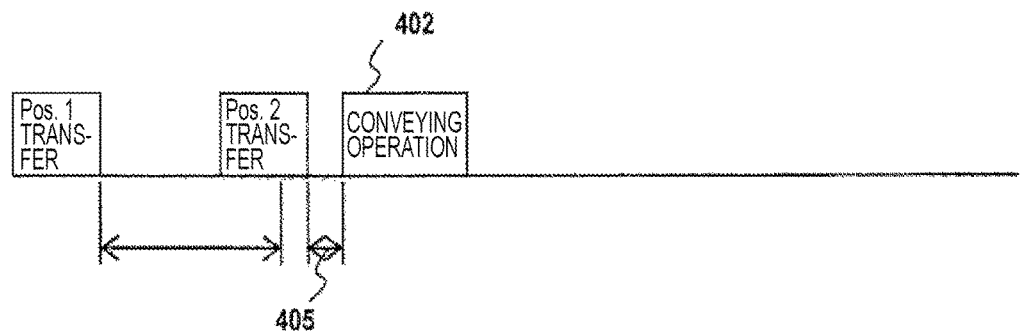
Figure 7:
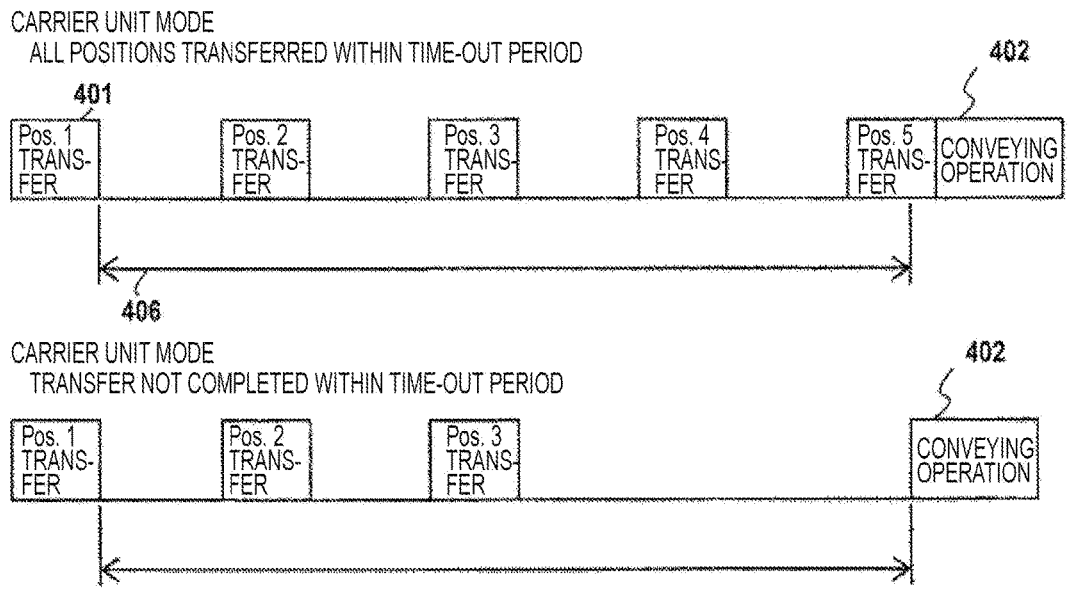
FIG. 7 is a diagram for describing operation of time-out control mode per carrier.

Next, a case where time-out is set will be described as a different embodiment, using FIGS. 6 and 7.

A specimen inside a specimen container 91 to be transferred is liquid collected from a human body. That is to say, in the case where the specimen is left for a long period, evaporation of the specimen may be caused. When the specimen is evaporated, concentration becomes high and an appropriate measurement result cannot be obtained, and in the worst case, measurement of relevant items cannot be executed and there is a possibility that blood has to be collected again. Further, leaving the specimen for a long time delays a timing to start the measurement in the analyzing system, and this may delay a result reporting to a patient as well.

In view of the above situation, time-out is set per transference of each specimen. Time-out control is executed every time the specimen is placed, and when a time exceeds a time-out period, conveyance to an analyzing system is to be started even though the carrier is not fully loaded.

A plurality of methods may be assumed for this time-out control. For example, there is a method whereby the time-out control is executed per specimen holding position on the carrier (time-out control mode per specimen unit). In this case, in each of successive specimen holding positions, a time between transferring a specimen container to a specimen holding position and transferring the specimen container to a next specimen holding position is controlled by a fixed time such that the carrier is conveyed when a waiting time exceeds the fixed time.

There is another time-out control method whereby time-out control method may be executed per carrier unit (time-out control mode per carrier). In this case, a time point of executing an initial specimen transfer to the carrier is set as a starting point of the time-out control, so that when a time exceeds the preliminarily set fixed time, the carrier is conveyed before all of specimen holding positions of the carrier are fully loaded.

The former time-out control mode per specimen unit will be described, using FIG. 6.

A time point of completing specimen placement 401 for every specimen holding position on the carrier is set as a starting point of the time-out, and a start of the specimen placement 401 for a next position is set as an ending point of the time-out.

For instance, a description will be given for the case where the fixed time for the time-out control is set such that the specimen container is placed in the next position within 10 seconds to execute the time-out control. When the next specimen placement 401 is started within 10 seconds after completion of the former placement operation, the time-out control is invalidated. When the specimen placement 401 for a next position is not started within the time-out period, a conveying operation 402 is started, determining the situation as time-out.

It is possible to set the time-out period for each specimen, and a time-out value can be differentiated between a specimen with high urgency and a specimen with low urgency. In other words, in the case of the specimen with high urgency, the fixed time for the time-out control may be set to three seconds, thereby achieving the operation prioritizing urgency.

The latter time-out control mode per carrier unit will be described, using FIG. 7. Completion of the specimen placement 401 for a head position is set as a starting point of the time-out period, and full-load of the carrier is set as an ending point of the time-out.

For instance, a description will be given for a case where a transferring time for an entire carrier is set to 30 seconds as the fixed time for the time-out control. When the specimen placement 401 for all of the positions is executed within 30 seconds after completion of placing the first specimen container in the carrier, the time-out control is invalidated. Of course, even when the time-out is invalidated, the conveying operation 402 is executed because the carrier is fully loaded.

In the case where 30 seconds has passed before a next specimen container is transferred to a position 4 or thereafter, the conveying operation 402 is started in a state where the specimens are placed only up to a position 3.

According to this function, an interval of feeding a carrier to an analyzing system can be controlled constant, and deterioration of the specimen caused by replacement of the carrier can be prevented.

Fourth Embodiment

Next, a carrier transferring method that facilitates bar code information reading will be described as a different embodiment.

In a general analyzing system, bar code information 92 pasted on a specimen container 91 placed on a carrier 71 is read to recognize a content of processing of a specimen. However, in the case where the carrier 71 is formed of a rack including a plurality of positions, more specifically, in the rack where five specimen containers 91 can be placed, orientation of the specimen containers, where the bar code information 92 can be read, is limited. In this case, when there is a mechanism that rotates the specimen containers 91 held by the carrier 71, the bar code information can be read by rotating the specimen containers in an appropriate direction. However, in the case where such a mechanism is not provided in an analyzing system, the bar code information cannot be read and analysis cannot be executed. Therefore, in such an analyzing system, what is desired is that the orientation of the specimen containers 91 is uniformly set such that the bar code information can be read when the specimen containers 91 are transferred to the carrier 71 by the transfer device.

Since a rotation mechanism 21 is provided at a specimen transfer source position 81 of the transfer device, the bar code can be read while rotating the specimen container 91. The rotation is stopped at the time point when the bar code is read, and therefore the specimen containers can be uniformly set such that the specimen bar codes are oriented in the same direction (in this case, the rotation is stopped with the bar code oriented on the front side).

Keeping this state, the specimen containers 91 are removed by a transfer X-Y-Z mechanism 111 and a chuck mechanism 112 and then placed on the carrier 71. Therefore, when the specimen containers are conveyed to the analyzing system, the specimen containers can be conveyed with the specimen bar code information 92 uniformly oriented. Accordingly, the specimen bar code can be read in the analyzing system without rotating the specimens.

Fifth Embodiment

Figure 5:
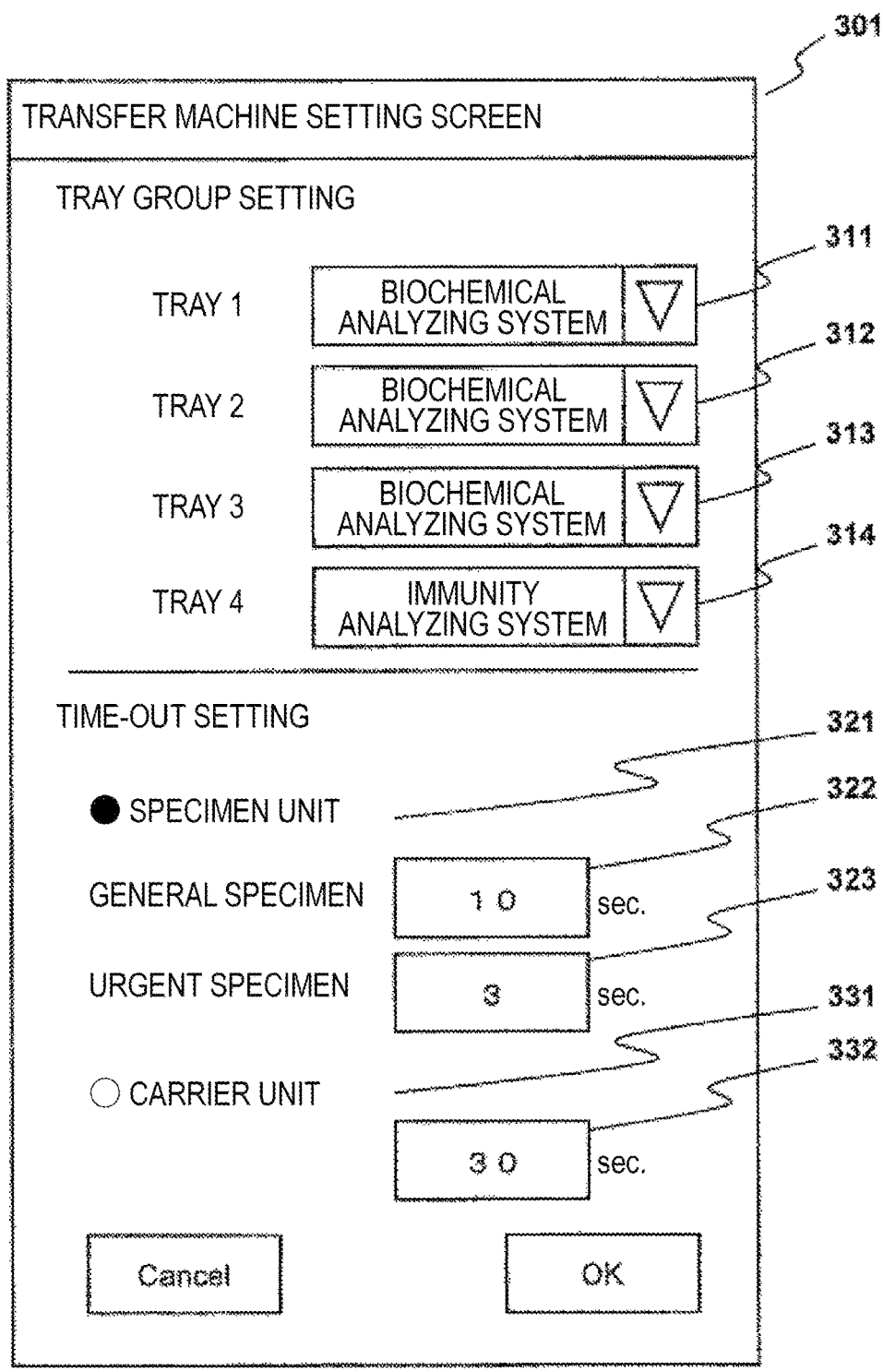
FIG. 5 is a diagram illustrating a screen for registering settings for a transfer machine according to the present invention.

A system including a screen whereby settings for the present invention can be executed will be described as a different embodiment, using FIG. 5.

Group setting for each tray as well as time-out setting can be set by using a transfer machine setting screen 301.

A group to belong can be selected for each of trays, using tray group setting list boxes 311, 312, 313 and 314. According to the present embodiment, trays 1 to 3 are set to convey specimen containers to a biochemical analyzing system and a tray 4 is set to convey specimen containers to an immunity analyzing system. The grouping is not limited to the groups described in this embodiment. In the case where plural kinds of clinical examination devices are connected to a pretreatment system, grouping the trays for each kind of the clinical examination devices is required to be possible at least. Also, the control according to the present invention is not limited to the connection from the pretreatment system to the analyzing system, and the present invention is preferably executed in a case of performing replacement of carriers in an examination system connected to a system where a different type of carrier is used.

Additionally, in terms of time-out control for transference, a unit used for time control can be changed by time-out setting mode toggle switches 321 and 331. At this point, a time-out value can be also input at time-out input boxes 322, 323 and 332.

The setting screen is displayed on a control CRT5 whereby settings for the pretreatment system or the clinical examination device are executed, and an operator executes such settings with a keyboard 4 or the like.

Six Embodiment

There is still another embodiment in which a carrier bar code reader 52 may be provided at each transfer position 82 so as to read bar code information of a carrier 71 before executing transferring operation for a specimen. In this case, it is necessary to provide the carrier bar code reader 52 in each tray; however, the bar code information of the carrier 71 can be identified before transferring operation even without configuring a conveyance line 51 for transfer destination carrier to move bidirectionally.

REFERENCE SIGNS LIST

1 Microcomputer
2 Memory used by microcomputer
3 External storage medium
4 Keyboard
5 Display
6 Interface
11 Conveyance line for transfer source carrier
12 Stopper for transfer source carrier
21 Specimen container rotation device
22 Specimen bar code reader
31, 32, 33, 34 Trays for transfer destination carrier
41, 42, 43, 44 Detectors for transfer destination carrier
45, 46, 47, 48 Pushing-back mechanisms
51 Conveyance line for transfer destination carrier
52 Bar code reader for transfer destination carrier
53 Handover position for transfer destination carrier in analyzing device
54 Waiting position for transfer destination carrier
55 Carrier conveyance mechanism
61 Transfer source carrier
71 Transfer destination carrier
72 Carrier bar code
81 Removal position of transfer source specimen container
82 Placement position of transfer destination specimen container 91 Specimen container
92 Specimen bar code
111 Transfer X-Y-Z mechanism
112 Chuck mechanism
201 Specimen transfer device
202 Pretreatment system
203 Conveyance line system
204-1, 204-2, 205 Analyzing systems
301 Transfer machine setting screen
311 Group setting for tray 1
312 Group setting for tray 2
313 Group setting for tray 3
314 Group setting for tray 4
321 Time-out setting mode toggle switch, Specimen unit mode
322 Time-out setting for general specimen transfer interval
323 Time-out setting for transfer interval urgent specimen
331 Time-out setting mode toggle switch, Carrier unit mode
332 Carrier unit time-out period
401 Transferring operation
402 Conveying operation
403 Time-out period between placement of general specimens
404 Exceeding Time-out period between placement general specimens
405 Time-out period between placement of urgent specimens
406 Time-out period per carrier unit
501 Operation time in which 10 specimens are successively transferred by setting one tray to one group
502 Operation time in which 10 specimens are successively transferred by setting two trays to one group
503 Operation difference

The invention claimed is:

1. A specimen transfer device, comprising:
a plurality of trays, each configured to hold one or more carriers, each carrier has barcode information and is configured to hold one or more specimen containers;
a transfer mechanism including a chuck configured to transfer a specimen container to a carrier on a tray of the plurality of trays;
a conveyance line configured to convey carriers bi-directionally;
a first barcode reader configured to read barcode information of carriers conveyed by the conveyance line to the first barcode reader;
a carrier conveyance mechanism on the conveyance line configured to convey carriers on the conveyance line; and
a computer connected to the transfer mechanism, the first barcode reader, and the carrier conveyance mechanism, the computer programmed to:
define a group of trays that consists of two or more trays that are allocated to an analysis system,
control the transfer mechanism to continuously transfer specimen containers to a first carrier on a first tray of the group,
during the transfer of the specimen containers to the first carrier on the first tray of the group by the transfer mechanism:
control the carrier conveyance mechanism to convey a second carrier from a second tray of the group to the first barcode reader on the conveyance line,
control the first barcode reader to read the barcode information from the second carrier conveyed by the carrier conveyance mechanism,
after reading the barcode information by the first barcode reader, control the carrier conveyance mechanism to convey the second carrier to the second tray from the first barcode reader,
after the second carrier is conveyed to the second tray, control the transfer mechanism to continuously transfer specimen containers to the second carrier on the second tray,
during the transfer of the specimen containers to the second carrier on the second tray of the group by the transfer mechanism, control the conveyance line to convey the first carrier from the first tray to a standby position on the conveyance line, which is at a different position on the conveyance line than positions of each of the trays on the conveyance line and the first barcode reader.

2. The specimen transfer device according to claim 1, wherein the computer is further programmed to:
determine if a carrier on a tray is fully loaded with specimen containers,
and switch a transfer destination tray of the transfer mechanism to a different tray than the tray having the fully loaded carrier that is allocated to a same group than the tray having the fully loaded carrier is allocated.

3. The specimen transfer device according to claim 1, wherein the computer is further programmed to: switch a transfer destination tray of the transfer mechanism to a different tray of a same group in a case where there is no new specimen container to be transferred by the transfer mechanism within a predetermined time.

4. The specimen transfer device according to claim 3, further comprising a user interface connected to the computer,
wherein the computer is programmed to: accept an input via the user interface to change the predetermined time depending on a priority level of a specimen.

5. The specimen transfer device according to claim 1, wherein the computer is further programmed to:
determine that a tray is empty with respect to specimen carriers, and
control the transfer mechanism to transfer a next specimen container to be transferred to a carrier on a tray other than the tray that is empty that is of a same group.

6. The specimen transfer device according to claim 1, further comprising a second barcode reader configured to read a specimen barcode disposed on a specimen container that is disposed at a transfer source position of the transfer mechanism, the transfer source position retaining a specimen container to be transferred to a carrier by the transfer mechanism.

7. The specimen transfer device according to claim 6, further comprising a rotation mechanism configured to rotate the specimen container at the transfer source position that retains the specimen container to be transferred to the carrier by the transfer mechanism.

8. The specimen transfer device according to claim 7, wherein the computer is programmed to:
control the rotating mechanism to rotate the specimen container and simultaneously control the second barcode reader to read the specimen bar code disposed on the specimen container, and stop the rotation by the rotating mechanism at a position where the specimen barcode is read by the second barcode reader.

9. The specimen transfer device according to claim 1, further comprising a pretreatment system,
wherein a specimen container transferred by the transfer mechanism is transferred from a transfer source position within the pretreatment system that pretreats a specimen held in the specimen container,
a pretreatment carrier of the pretreatment system, which is different than the one or more carriers, is configured to hold only one specimen container, and the one or more carriers to which the transfer mechanism transfers a specimen container is configured to hold more than one specimen containers.

10. A method of transferring specimens by a specimen transfer device, comprising:
   a plurality of trays, each configured to hold one or more carriers, each carrier has barcode information and is configured to hold one or more specimen containers;
   a transfer mechanism including a chuck configured to transfer a specimen container to a carrier on a tray of the plurality of trays;
   a conveyance line configured to convey carriers bi-directionally;
   a first barcode reader configured to read barcode information of carriers conveyed by the conveyance line to the first barcode reader;
   a carrier conveyance mechanism on the conveyance line configured to convey carriers on the conveyance line; and
   a computer connected to the transfer mechanism, the first barcode reader, and the carrier conveyance mechanism, the method comprising:
   defining, by the computer, a group of trays that consists of two or more trays that are allocated to an analysis system;
   controlling the transfer mechanism to continuously transfer specimen containers to a first carrier on a first tray of the group;
   during the transfer of the specimen containers to the first carrier on the first tray of the group by the transfer mechanism:
      controlling the carrier conveyance mechanism to convey a second carrier from a second tray of the group to the first barcode reader on the conveyance line;
      controlling the first barcode reader to read the barcode information from the second carrier conveyed by the carrier conveyance mechanism;
      after reading the barcode information by the first barcode reader, controlling the carrier conveyance mechanism to convey the second carrier to the second tray from the first barcode reader;
   after the second carrier is conveyed to the second tray, controlling the transfer mechanism to continuously transfer specimen containers to the second carrier on the second tray;
   during the transfer of the specimen containers to the second carrier on the second tray of the group by the transfer mechanism, controlling the conveyance line to convey the first carrier from the first tray to a standby position on the conveyance line, which is at a different position on the conveyance line than positions of each of the trays on the conveyance line and the first barcode reader.

* * * * *